(12) United States Patent
Robin

(10) Patent No.: US 7,779,672 B2
(45) Date of Patent: Aug. 24, 2010

(54) METHOD AND DEVICE FOR MEASURING THE MINIMUM MISCIBILITY PRESSURE OF TWO PHASES

(75) Inventor: Michel Robin, Poissy (FR)

(73) Assignee: IFP, Rueil Malmaison Cedex (FR)

( * ) Notice: Subject to any disclaimer, the term of this patent is extended or adjusted under 35 U.S.C. 154(b) by 259 days.

(21) Appl. No.: 11/873,444

(22) Filed: Oct. 17, 2007

(65) Prior Publication Data

US 2008/0173076 A1    Jul. 24, 2008

(30) Foreign Application Priority Data

Oct. 19, 2006    (FR) .................................. 06/09.261

(51) Int. Cl.
*G01N 7/00*    (2006.01)
(52) U.S. Cl. ........................ 73/29.01; 29/237
(58) Field of Classification Search ............... 73/29.01, 73/23.3
See application file for complete search history.

(56) References Cited

U.S. PATENT DOCUMENTS 4,455,860 A    6/1984 Cullick et al. .............. 73/19.11
4,621,522 A * 11/1986 Christiansen et al. ...... 73/61.41
4,627,273 A   12/1986 Christiansen et al. ...... 73/61.78
5,505,074 A    4/1996 Mihcakan et al. .......... 73/64.45

OTHER PUBLICATIONS

International Search Report; FR 0609261; Jun. 5, 2007.
Rao D.N, "New Technique of Vanishing Interfacial Tension for Miscibility Determination" Fluid Phase Equilibria, Jun. 1997, vol. 139, pp. 311-324.

* cited by examiner

*Primary Examiner*—Hezron Williams
*Assistant Examiner*—Tamiko D Bellamy
(74) *Attorney, Agent, or Firm*—Antonelli, Terry, Stout & Kraus, LLP.

(57) ABSTRACT

The invention is a method and device for measuring the minimum miscibility pressure of two phases having application for enhanced oil recovery or $CO_2$ geologic storage. In a pressure cell, gas is bubbled into a liquid, or conversely, liquid is dripped into a gas. The presence of bubbles or of drops is detected through the differential pressure variation measured between the inside of the cell and an injected phase injection line. This measurement is performed by means of a very accurate differential pressure sensor, for various pressures imposed within the cell. A relation between the number of bubbles or of drops formed per time unit and pressures within the cell is deduced therefrom. The minimum miscibility pressure of the two phases then corresponds to the pressure for which the inverse of the number of bubbles or of drops is zero, which is deduced by extrapolation of the relation.

6 Claims, 3 Drawing Sheets

METHOD AND DEVICE FOR MEASURING THE MINIMUM MISCIBILITY PRESSURE OF TWO PHASES

BACKGROUND OF THE INVENTION

1. Field of the Invention

The invention relates to the technical field of minimum miscibility pressure determination methods.

2. Description of the Prior Art

When gas is to be injected into an oil-containing reservoir, an important parameter to be taken into account is the minimum miscibility pressure of oil and gas. This pressure, referred to as MMP (Minimum Miscibility Pressure), is the pressure above which gas and oil become miscible. The value of this MMP is fundamental because it determines the recovery ratio of the oil in place: a low miscibility leads to unstable displacements, fingering and therefore poor recovery. In the opposite case, that is a miscible displacement, oil recovery is nearly total in the zones, which are effectively swept. More generally, it is very important to know this parameter for simulation of the gas/oil displacements in reservoirs. Currently, this issue can be of special importance, notably linked with $CO_2$ geologic storage. In fact, the injection conditions and the stored amounts will be greatly influenced by this parameter.

There is therefore a need, particularly in the energy industry, to develop methods allowing fast and accurate measurement of the minimum miscibility pressure (MMP).

In practice, measuring this pressure is long and expensive. A conventional approach carries out several experiments of oil displacement by gas in porous media, at increasing pressures, and in analyzing the results in terms of recovery. In order to obtain the value of this parameter, various procedures are possible. The state of the art can be illustrated by the following document, which compares four known methods of measuring the minimum miscibility pressure (MMP):

Thomas, F. B.; Zhou, X. L.; Bennion, D. B.; Bennion, D. W., "A Comparative-Study of Rba, P-X, Multicontact and Slim Tube Results", Journal of Canadian Petroleum Technology-33/2 17-26 (0021-9487) (1994).

Pseudoternary Diagrams

It is possible to use pseudoternary diagrams, but determination of these diagrams requires time-consuming experimentations because, on the one hand, equilibria take a long time to obtain and, on the other hand, the results can depend on the path used to reach these equilibria. Furthermore, this method requires arbitrary fractionation of the oil to pseudocomponents, which are not always easy to determine.

Slim Tube Test (STT) Method

A second method sweeps an oil-saturated porous medium with gas, at different increasing pressures. Because of the mobility contrast between the gas phase and the oil phase, the displacement is intrinsically unstable and generates fingering. In order to overcome this difficulty, the injections are carried out at very low flow rates, and porous media of great length and small diameter (hence the designation Slim Tube Test) are used. The test itself carries out displacements at increasing pressures and in studying the oil recovery as a function of the pressure. This recovery increases more or less linearly as a function of the pressure and it eventually reaches a plateau value corresponding to a recovery ratio close to 100%. The value of the minimum pressure for reaching this plateau is the MMP to be determined. This technique is relatively simple but it takes a very long time because of the many displacement experiments that have to be carried out at a low flow rate.

Vanishing Interfacial Tension Method (VIT)

A different approach based on an interfacial tension measurement has recently appeared in the literature. Various authors have started examining this scientific problem. Rao and Takabayashi can be mentioned essentially.

Rao D. N, A New Technique of Vanishing Interfacial Tension for Miscibility Determination, Fluid Phase Equilibria, 1997, vol. 139, pp 311-324.

Takabayashi, K., Ohta, T., Okatsu, K, Interfacial Tension Measurement between Oil and Gas Phase under High Temperature and High Pressure Condition—Effect of Pressure on Interfacial tension and Comparison of Minimum Miscible by Vanishing Interfacial Tension Technique and Slim Tube Test. 25th Annual Workshop & Symposium. Stavanger, Norway, Sep. 5-9, 2004

When two bodies are miscible, the interfaces no longer exist and this property is expressed by a vanishing interfacial tension (IFT). This property is then used to determine the MMP, the interfacial tension is measured as a function of the pressure and the minimum pressure for which the IFT vanishes is thus determined. This technique is definitely faster but it however involves some drawbacks. First of all, measuring the IFT requires knowledge of the density of the two phases under the experimental conditions. It takes a long time and delicate work that requires precise control of the experimental parameters (essentially pressure, temperature and volume ratio between the gas phase and the oil phase). It can furthermore be noted that the closer one gets to miscibility, the longer the time required to reach the thermodynamic equilibria. Finally, and above all, the lower the interfacial tension, the more it is difficult and delicate to measure.

One of the problems associated with measurement by VIT is linked with the equilibrium conditions and the determination of the densities. Close to miscibility, the densities become very close to one another. Now, IFT measurement is directly proportional to the difference between these densities. Therefore, the closer the latter are to one another, the more the error on the density determination leads to a serious error on the IFT determination.

SUMMARY OF THE INVENTION

The invention is a method allowing measurement of the minimum miscibility pressure of two phases, a liquid and a gas phase, wherein the two phases are placed in a cell under a given pressure (P). The method comprises the following stages:

a) injecting one of the phases into the cell through an injection line, at a given flow rate (Q) so as to form globules, such as liquid drops or gas bubbles, of the injected phase in the other phase, and discharging the injected phase from the cell at a second flow rate allowing the cell to be maintained at a constant pressure (P);

b) determining a number (N) of globules of the injected phase per time unit, by continuous measurement of the differential pressure (DP) between the inside of the cell and the injection line;

c) establishing, for the given flow rate (Q), a function f relating the inverse of the number (N) of globules of the injected phase per time unit to the pressure (P) within the cell, by varying pressure (P) within the cell and by repeating stages a) and b) for each pressure; and d) estimating the minimum miscibility pressure of the two phases by a pressure (P) within the cell for which function f is equal to zero.

According to the invention, the liquid phase may be indiscriminately injected into the gas phase, with the globules being drops in this case, or conversely inject the gas phase into the liquid phase, with the globules being then bubbles.

The method according to the invention is a faster approach than the prior methods and it allows, among other things, overcoming the aforementioned problems, such as the necessity to know parameters relative to the phases (density, composition, . . . ) and the necessity to measure with precision the interfacial tension.

The invention also is a device allowing measurement of the minimum miscibility pressure of two phases, a liquid and a gas phase, comprising at least a first pump (P1, P3) allowing one of the phases (LIQ, G) to be injected into a cell (CEL) by an injection line connected to one end of cell, a means (B) for injecting the other phase and a pressure sensor (CP) measuring the pressure within the cell. The device includes the following elements:

the injection line comprises a capillary (CAP) whose length and diameter produce globules of the phase injected into the other phase;

means for maintaining the pressure within the cell (P2, P3) constant; and a differential pressure sensor (CPD) located between the capillary (CAP) and the cell (CEL).

The means for maintaining the pressure within the cell (P2, P3) constant can comprise a second pump (P2) for discharging the injected phase at the end of the cell opposite the injection end.

The device can further comprise means (P3) for preventing a delay of the miscibility phenomenon between the phases. These means can comprise a pump (P3) for discharging the injected phase at the end of the cell opposite the injection end and for re-injecting it by means of the capillary at the injection end.

The device according to the invention does not require a dedicated equipment (such as the equipment used in methods that require observing the shape of a drop through portholes), which are both very complex and very expensive.

BRIEF DESCRIPTION OF THE DRAWINGS

Other features and advantages of the method and of the device according to the invention will be clear from reading the description hereafter of embodiments given by way of non imitative examples, with reference to the accompanying figures wherein.

DETAILED DESCRIPTION OF THE INVENTION

The method according to the invention allows measurement of the minimum miscibility pressure, referred to as MMP by specialists, between a gas and a liquid. It is based on a technique utilizing on interfacial tension. According to the method, gas is bubbled into the liquid phase, or conversely liquid is dripped into the gas phase, and the presence of bubbles or of drops is detected through the differential pressure variation measured by a highly accurate differential pressure sensor. The pressure variations induced by the formation of these drops or of these bubbles are very low, a few millibars at the most. This sensor however has to operate under a high line pressure (of the order of some hundred bars).

Figure 2:
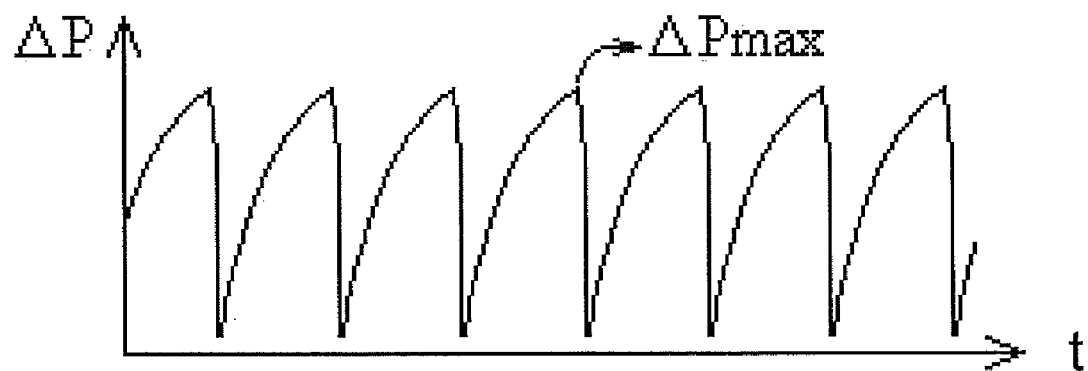
FIG. 2 shows a recording of a differential pressure variation ($\Delta P$) as a function of time (t), during a bubbling process.

For given thermodynamic conditions, a given equipment, and while disregarding the dynamic phenomena, the volume of the drops formed only depends on the interfacial tension. FIG. 2 illustrates the possibility, for a given flow rate, of measuring the number of drops formed per time unit (each drop corresponds to each differential pressure peak $\Delta Pmax$). The volume of the drops is however directly proportional to the interfacial tension. Therefore, for a given flow rate, by measuring the number of drops formed per time unit, it is possible to know the volume of these drops. From the evolution of this volume as a function of the pressure, it is possible to go back to the evolution of the interfacial tension, without requiring complete measurement of this interfacial tension. It is then no longer necessary to precisely know the composition of the phases or the density thereof. This method is thus much faster than the prior methods. The method mainly comprises three stages:

1—injecting one of the phases (liquid or gas) into the other phase, by a capillary, at a given flow rate and pressure;

2—counting the number of drops or of bubbles of the injected phase per time unit as a function of the flow rate and of the pressure; and 3—deducing therefrom the minimum miscibility pressure of the two phases.

According to a particular embodiment, the invention is described within the context of the injection of a liquid into a gas. The method according to the invention can however be indiscriminately carried out in both directions: either by dripping drops of liquid into the gas phase, downwards, or by causing gas bubbles to rise in the liquid phase, upwards. Thus, within the context of the injection of a liquid in a gas, globules of liquid form and, within the context of the injection of gas in a liquid, globules of gas form. What are referred to as globules are either a spherical or a spheroidal body of small dimension.

1—Injection of a Liquid in Gas at a Given Flow Rate and Pressure

The liquid and the gas to be studied are placed in a cell of about 150 $cm^3$ under isothermal conditions, a drying oven for example. The cell can withstand the pressure and temperature conditions under which the measurements are to be performed. It can also withstand the corrosion due to the products used. This cell is provided with a pressure sensor (CP) for monitoring the pressure within the cell. The resistance conditions of this sensor are different from those of the cell: the sensor withstands the experimental pressure, but it can be arranged outside the drying oven, at ambient temperature. This sensor can preferably withstand a line pressure of the order of 500 bars and a full-scale measuring range of some ten millibars.

This cell is pressurized and its temperature is controlled. Pressurization is performed by injecting a gas (G) using a pressurized bottle (B) or a pump. Typically, the temperature can range from ambient temperature to about 200° C., and the pressure can be up to approximately 500 bars. These thermodynamic conditions are specific to each fluid pair to be studied. In the petroleum field, for example, the temperature is that of the reservoir for which these measurements are carried out, and the pressure evolves, starting from the reservoir pressure until miscibility is obtained.

One waits for thermodynamic equilibrium to be reached, that is no more transfer between the liquid phase and the gas phase. Typically, this corresponds to a constant pressure in the measuring cell.

Figure 1:
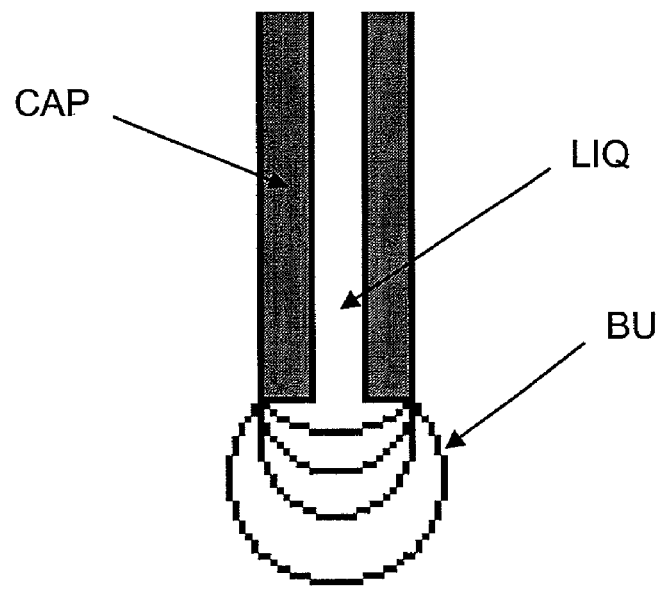
FIG. 1 illustrates the formation of a bubble (BU) of a liquid (LIQ) at the outlet of a capillary (CAP)

Liquid is pushed into the cell at a given flow rate, by a pump (this pump provides, without any pressure surge, injection of a fluid at a known and constant flow rate). This liquid drips at the end of a capillary. FIG. 1 illustrates the formation of a bubble (BU) of a liquid (LIQ) at the outlet of a capillary (CAP).

Simultaneously, a second pump of the same type as the first one discharges liquid from the cell, approximately at the same flow rate, in order to maintain the cell at a constant pressure. The flow rate conditions correspond to a flow that has to be a dropwise flow, fast enough for the experiment not to last too long, and slow enough for the fluids to be assumed to remain at equilibrium in the cell. Typically, the injection rate ranges between 0 and 50 cm$^3$/h. The capillary can be made of glass or of metal. Its length will be small enough not to cause too great a pressure drop and not to disturb the measurement. Typically, a capillary of about 2-3 cm in length and of a diameter below one millimeter is selected. The thinner the capillary, the more accurate the measurement, but the more it is difficult and the more there are clogging risks.

2—Counting the Number of Drops Per Time Unit

Every time a drop appears at the end of the capillary and falls off, there is a slight pressure variation in the injection line arranged upstream from the capillary, which is detected by means of a differential pressure sensor located between the injection line and the cell. For a given flow rate, the drops occur at regular intervals.

It is thus possible to count the number of drops formed per time unit, for a given liquid injection rate and pressure within the cell. FIG. 2 illustrates the pressure variation in the injection line (differential pressure ΔP between the inside of the cell and the injection line over time t), measured by the differential pressure sensor, for a given flow rate Q and a given pressure P within the cell. Each decrease corresponds to a dripping drop. It is therefore easy to measure the number of drops formed per time unit, for a given flow rate Q and a given pressure P within the cell: the number of drops corresponds to the number of differential pressure ΔPmax peaks.

3—Determination of the Pressure at Which the Interfacial Tension is Zero

This operation is repeated (at least twice) for several increasingly high pressures within the cell. The pressure is imposed by the gas injection in the cell. In the petroleum field, for example, the temperature is that of the reservoir for which these measurements are performed, and the pressure evolves starting from the reservoir pressure until miscibility is obtained. For each pressure stage within the cell, we thus obtain (pressure/number of drops) pairs:

$(P(Q)^1, N(Q)^1), (P(Q)^2, N(Q)^2), (P(Q)^3, N(Q)^3), \ldots$

It is thus possible, for a given flow rate Q, to draw a curve f representing a relation between the inverse of the number of drops per time unit (N), which is measured by the differential pressure sensor, and the pressure within the cell:

$$\frac{1}{N(Q)} = f(P).$$

Figure 3:
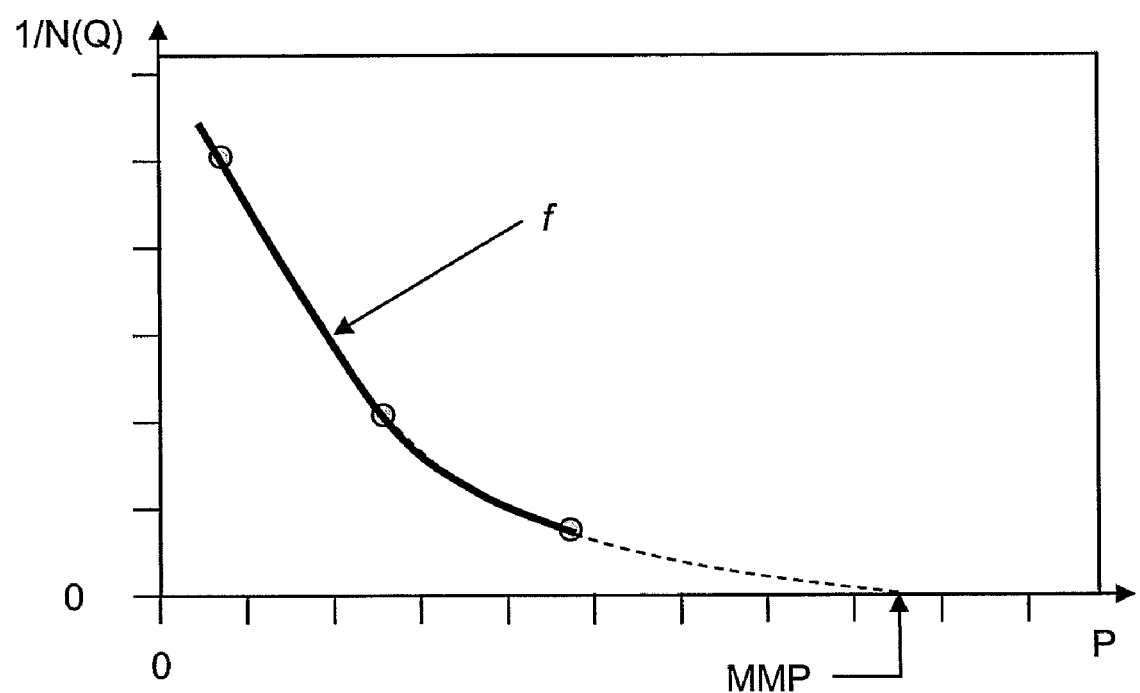
FIG. 3 illustrates, for a given flow rate, the determination of the pressure at which the interfacial pressure, that is pressure MMP, is zero.

Such a curve is diagrammatically shown in FIG. 3.

According to the method, the pressure P is sought for which there is miscibility between the liquid and the gas, that is when the interfacial tension is zero.

When the interfacial tension is zero, the volume of the drops is zero. In fact, for each stage, the volume V of the drops formed is directly proportional to the liquid/gas interfacial tension denoted by $T_{int}$. In fact, at equilibrium, the weight of the suspended drop is balanced by the interfacial tension, and the weight is directly proportional to the volume of the drop. Thus, for a zero interfacial tension, the volume of the drop is zero.

In practice, for thermodynamic equilibrium reasons, we wait for the volume of the drops to be stabilized for each stage.

For a single flow rate Q, the number of drops per time unit (or per volume unit) is inversely proportional to the interfacial tension. In fact, the higher the interfacial tension, the more the drops will have difficulty falling: at equilibrium, the weight of the suspended drop is balanced by the interfacial tension. Therefore, for the same time interval and the same flow rate, the number of drops is larger in the case of a low interfacial tension than in the case of a high interfacial tension. Thus, for the given flow rate Q and a given pressure P, it can be written:

$$\frac{1}{N(Q, P)} = b \cdot T_{int}$$

with N the number of drops per time unit for a given flow rate Q and a given pressure P, b a factor and $T_{int}$ the liquid/gas interfacial tension.

Thus, when the interfacial tension is zero, the inverse of the number of drops is also zero.

By extending curve f, $$\frac{1}{N(Q)} = f(P),$$

so as to intersect the abscissa axis $$\left(\frac{1}{N(Q)} = 0\right),$$

the pressure P is determined for which the interfacial pressure is zero.

FIG. 3 illustrates the extrapolation of curve f (dotted curve) and the determination of the pressure at which the interfacial tension is zero (MMP). Extrapolation can be carried out by means of a linear regression if the relation between the variation of 1/N(Q) as a function of P seems to be linear, or by means of any other extrapolation method (polynomial regression, . . . ) if the relation is not linear.

This pressure corresponds to the minimum miscibility pressure.

Figure 4:
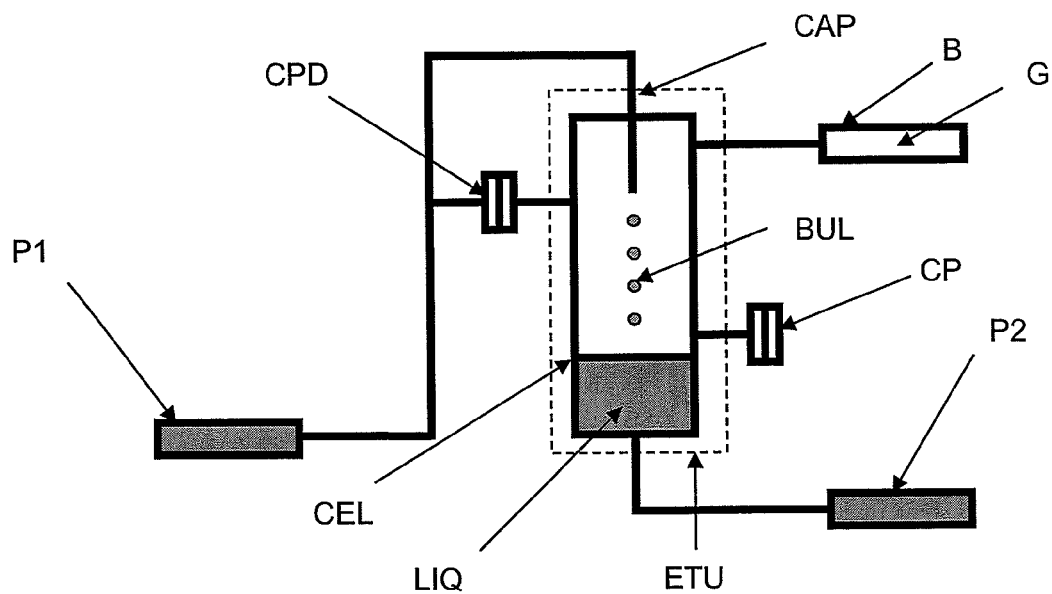
FIG. 4 is a diagram of a device allowing the method according to the invention to be implemented.

The device allowing the method according to the invention to be implemented is illustrated in FIG. 4. This device comprises a pump (P1) allowing a liquid (LIQ) to be injected into an isothermal cell (CEL) by a capillary (CAP) that is connected to one end of the cell (the top of the cell within the context of an injected liquid and bottom of the cell within the context of an injected gas). The drops of liquid (BUL) that form at the outlet of capillary (CAP) fall into cell (CEL) and they are sucked by a pump (P2) arranged at the other end of cell (CEL). The cell contains, in addition to the liquid (LIQ), a gas (G) injected into the cell by a pressurized bottle (B) so as to impose a pressure P inside. A differential pressure sensor (CPD) is arranged between capillary (CAP) and cell (CEL). The cell can be placed in a drying oven (ETU). Finally, a pressure sensor (CP) measures the pressure within the cell. It can be arranged outside the drying oven.

Figure 5:
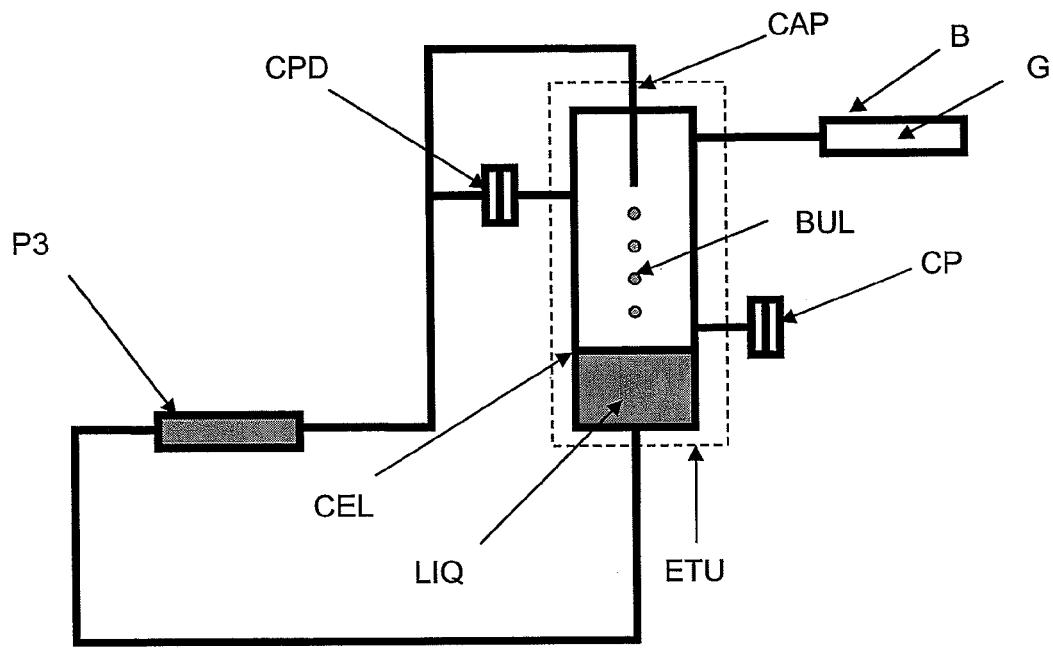
FIG. 5 is a diagram of an improved device according to the invention.

FIG. 5 shows an improvement brought to the device according to the invention. This improvement replaces the two pumps P1 and P2 by a single pump P3 that then provides recirculation of the liquid that can be discharged at the bottom of the cell so as to be re-injected by the capillary. The advantage of this technique is that the fluids have a better thermodynamic equilibrium. In fact, in this case, a liquid that has already been in contact with the gas that is injected into the cell. This improvement overcomes the partial miscibility phenomenon that occurs prior to the miscibility phenomenon. In fact, when a liquid is in contact with a gas, there is a first phase during which part of the liquid passes into the gas phase, whereas part of the gas passes into the aqueous phase. This phase thus causes a "delay" or longer equilibrium times for the miscibility phenomenon to be measured. The first partial miscibility phase is avoided by injecting into the cell a liquid that has already been in contact with the gas.

The method according to the invention thus relates to a new technique for measuring the minimum miscibility pressure (MMP) allowing, on the one hand, saving significant time and, on the other hand, doing so without dedicated equipment (such as the equipment used in methods requiring observation of the shape of a drop through portholes), both of which are very complex and very expensive.

The method avoids having to know with precision the composition of the phases and the density thereof. The improved device furthermore allows more accurate measurement of the minimum miscibility pressure.

The method has industrial applications, for example in the petroleum industry, for the study of surface phenomena and of flows in porous media, and notably for the study of $CO_2$ geologic storage.

The invention claimed is:

1. A method for measuring the minimum miscibility pressure of a liquid and a gas phase, are placed in a cell under pressure, comprising:
    a) injecting one of the phases into the cell with an injection line, at a flow rate to form globules, comprising liquid drops or gas bubbles, of the injected one phase in the other phase, and discharging the injected phase from the cell at a second flow rate at which the cell is maintained at a constant pressure;
    b) determining a number of globules of the injected phase per time unit, by continuous measurement of differential pressure between an inside of the cell and the injection line;
    c) establishing, for the given flow rate, a function relating an inverse of the number of globules of the injected phase per time unit to pressure within the cell, by varying pressure within the cell and by repeating a) and b) for each pressure; and
    d) estimating the minimum miscibility pressure of the phases by pressure-within the cell for which the function is equal to zero.

2. A method as claimed in claim 1, wherein the liquid phase is injected into the gas phase and the globules are drops.

3. A method as claimed in claim 1, wherein the gas phase is injected into the liquid phase and the globules are bubbles.

4. A device for measuring minimum miscibility pressure of a liquid and a gas phase, comprising:
    at least a first pump for injecting one of the phases into a cell with an injection line connected to an end of the cell comprising a capillary having a length and diameter for producing globules of the phase injected into the other phase, means for injecting the other of the phases into the cell, a pressure sensor for measuring pressure within the cell, means for maintaining a constant pressure within the cell, a differential pressure sensor located between the capillary and the cell and means for preventing a delay of miscibility between the phases.

5. A device as claimed in claim 4, wherein the means for preventing a delay of miscibility between the phases comprises a pump for discharging the injected phase at an end of the cell opposite the end at which injection occurs and for re-injecting the discharged phase with the capillary at the end at which injection occurs.

6. A device for measuring minimum miscibility pressure of a liquid and a gas phase, comprising:
    at least a first pump for injecting one of the phases into a cell with an injection line connected to an end of the cell comprising a capillary having a length and diameter for producing globules of the phase injected into the other phase, means for injecting the other of the phases into the cell, a pressure sensor for measuring pressure within the cell, means for maintaining a constant pressure within the cell, and a differential pressure sensor located between the capillary and the cell, and wherein
    the means for maintaining constant pressure within the cell comprises a second pump for discharging the injected phase at an end of the cell at which the injection occurs.

* * * * *